United States Patent [19]

Tufano

[11] 4,287,372

[45] Sep. 1, 1981

[54] PREPARATION OF NITRO-SUBSTITUTED DIPHENYL ETHERS

[75] Inventor: Michael D. Tufano, Broadview, Ill.

[73] Assignee: UOP Inc., Des Plaines, Ill.

[21] Appl. No.: 83,925

[22] Filed: Oct. 11, 1979

[51] Int. Cl.³ ............................................ C07C 43/275
[52] U.S. Cl. ..................................... 568/635; 568/631
[58] Field of Search ................ 568/635, 628, 705, 631

[56] References Cited

U.S. PATENT DOCUMENTS

| | | | |
|---|---|---|---|
| 1,099,761 | 6/1914 | Ostermann | 568/635 |
| 3,487,114 | 12/1969 | Irick et al. | 568/635 |
| 3,567,783 | 3/1971 | Brown | 568/635 |
| 3,840,605 | 10/1974 | Gordan | 568/635 |

OTHER PUBLICATIONS

Dockx "Synthesis" 441 (1973).
McKillop et al., Terahedron, vol. 30, pp. 1379–1382.
Freedman et al., Tetrahedron Letters, No. 38, pp. 3251-3254, (1975), Perganon Press, Britain.

*Primary Examiner*—Werren B. Lone
*Attorney, Agent, or Firm*—James R. Hoatson, Jr.; Raymond H. Nelson; William H. Page, II

[57] ABSTRACT

A method of preparing nitro-substituted diphenyl ethers comprises contacting a salt of a phenol with a nitro-substituted halobenzene in the presence of a phase-transfer reagent under reaction conditions and recovering the reaction product.

5 Claims, No Drawings

PREPARATION OF NITRO-SUBSTITUTED DIPHENYL ETHERS

BACKGROUND OF THE INVENTION

Antioxidants are a class of additives which finds extensive use in various petroleum products. Antioxidants when used in lubricating oils need to have low volatility, and substituted diphenyl ethers may be used as antioxidants in lubricating oils. Important intermediates in the preparation of such antioxidants are nitro-substituted diphenyl ethers. The latter typically are prepared by the reaction of a phenolate with a nitro-substituted halobenzene. This reaction is characterized by modest yields of the desired product in a relatively impure state necessitating one or more subsequent purification steps.

SUMMARY

An object of this invention is to provide a method of preparing nitro-substituted diphenyl ethers in substantially greater yields and purity than heretofore possible. One embodiment of this invention is to prepare said ethers by the reaction of salts of phenols with nitro-substituted halobenzenes using phasetransfer catalysis. A more specific embodiment comprises the use of quaternary ammonium and quaternary phosphonium salts as phase-transfer reagents. Other objects and embodiments will be apparent from the more detailed description within.

DESCRIPTION OF THE INVENTION

In the usual synthesis of nitro-substituted diphenyl ethers a suitable salt of a phenol (phenolate) is reacted with a nitro-substituted halobenzene. This reaction typically is heterogeneous; the halobenzene is soluble in organic solvents but insoluble in water, whereas the phenolate may be soluble in water but insoluble in organic solvents. Solvents which potentiate a homogeneous reaction, e.g., hexamethylphosphoramide, dimethyl acetamide, and dimethyl sulfoxide, may have other disadvantages which make their use impractical for commercial preparation of the desired ethers, e.g., cost, difficulty of recovery, and suspected carcinogenic activity.

Phase-transfer catalysis is a technique of much interest in recent years. See J. Dockx, *Synthesis*, 441 (1973). In this process a reactant, called a phase-transfer reagent, when added to an aqueous phase forms an ion-pair with the ionic component present, e.g., phenolate. Because the formed ion-pair has appreciable solubility in organic solvents it is carried, at least in part, across the phase boundary from the aqueous to the organic phase, where it retains its identity as an ion-pair. This ion-pair in the organic phase then can react with another component dissolved in the organic phase to form the desired product. Because this reaction occurs homogeneously its rate is greater than when the reaction is conducted heterogeneously, and undesirable side reactions otherwise present may be diminished or even eliminated. After reaction, a different ion-pair is formed involving the phase-transfer reactant and this new ion-pair crosses from the organic into the aqueous phase where the phase-transfer reagent is again available to form an ion-pair with an ionic reactant in the aqueous phase, e.g., phenolate. Thus the phase-transfer reactant acts as a catalyst and needs to be employed in less than stoichiometric amounts.

A discovery of this invention is that when phase-transfer reagents are used in preparing nitro-substituted diphenyl ethers by reacting a phenolate with a nitro-substituted haloaromatic the desired product is formed in substantially higher yields and in substantially greater purity than when the conventional heterogeneous process is used.

The phase-transfer reagents used in this invention are quaternary ammonium and quaternary phosphonium salts. These can be written as $R_1R_2R_3R_4Z^+Y^-$, where Z is nitrogen or phosphorous and the R groups are alkyl or aralkyl groups containing from about 1 to about 20 carbon atoms. Illustrative examples of suitable alkyl and aralkyl groups include methyl, ethyl, propyl, butyl, pentyl, hexyl, heptyl, octyl, nonyl, decyl, undecyl, docecyl, tridecyl, tetradecyl, pentadecyl, hexadecyl, heptadecyl, octadecyl, nonadecyl, eicosyl, benzyl, methoxybenzyl, chlorobenzyl, 2-phenylethyl, 2-phenylpropyl, 3-phenylpropyl, 2-phenylbutyl, 3-phenylbutyl, 4-phenylbutyl, etc. Each of the R groups may be different, or 2 or more such R groups may be the same. The sole limitation is that the resultant quaternary ammonium or phosphonium compound be sufficiently lipophilic to be appreciably soluble in the organic phase. The nature of the anion, $Y^-$, is not critical, usually being a halide, such as chloride, bromide, or iodide. Chlorides often are preferred because of their availability. Other anions, such as bisulfate, nitrate, perchlorate, acetate, etc., may be used, although not necessarily with equivalent results. Such phase-transfer reagents are utilized in concentrations from about 1 to about 50 mole percent, but concentrations from about 1 to about 20 mole percent are preferred and concentrations from about 1 to about 10 percent are even more preferred.

Generally the phenol used in this invention is converted to a salt which typically is formed in situ. The salts of alkali metals are those most commonly employed, for example, lithium, sodium, potassium, cesium, and rubidium salts. These are formed by mixing the phenol with a solution of the alkali metal hydroxide, carbonate, or, in suitable cases, even the bicarbonates. However the method of forming such phenolates is not critical.

The phenols of this invention may bear a wide variety of substituents on the aromatic ring. Among the substituents which may be borne are alkyl, aryl, alkaryl, aralkyl, hydroxy, alkoxy, aryloxy, amino, alkylamino, dialkylamino, nitro, and alkylthio moieties and any combination of these moieties. The particular substituent employed and the number of such substituents may be dictated by the antioxidant properties of the diphenylether which is ultimately prepared. Examples of phenols which may be used, cited solely for illustration and not by way of limitation, include 2-methoxyphenol, 3-methoxyphenol, 4-methoxyphenol, 4-nitrophenol, 3-nitrophenol, 2-nitrophenol, 4-aminophenol, 4-methylaminophenol, 4-dimethylaminophenol, the cresols, 4-phenoxyphenol, 3-phenoxyphenol, 2-phenoxyphenol, 4-methylmercaptophenol, 4-ethylmercaptophenol, 4-phenylmercaptophenol, 2,4-dimethoxyphenol, 2-nitro-4-methoxyphenol, 4-methyl-2-methoxyphenol, 3-dimethylamino-4-nitrophenol, etc.

Just as a wide variety of substituted phenols may be used in this reaction, so also may a wide variety of nitro-substituted halobenzenes be employed. The only restriction is that the halobenzene be capable of undergoing nucleophilic substitution. The halogen of said halobenzene is most commonly chlorine, although bromine and iodine may be employed, but not necessarily with equivalent results. Among other substituents which may be present on the aromatic ring of the nitro-substituted halobenzene are alkyl, aryl, alkoxy, aryloxy, nitro, and alkylthio moieties and any combination of these where more than one substituent is present. Examples of such nitro-substituted halobenzenes, given by way of illustration only, are 4-nitrochlorobenzene, 4-nitrobromobenzene, 2,4-dinitrochlorobenzene, 2-methyl-4-nitrobromobenzene, 2-methoxy-4-nitrochlorobenzene, 4-nitro-3-phenoxychlorobenzene, 2,6-dimethyl-4-nitrochlorobenzene, 2-methylmercapto-4-nitrochlorobenzene, etc.

Typically the reaction is conducted at a temperature from about 50° to about 200° C. for a time varying between about 0.5 to about 20 hours, depending on the temperature used, the concentration of the phase-transfer reagent, and the nature of the phenolate and halobenzene. In the simplest process equimolar amounts of the phenol and the nitro-substituted halobenzene are mixed with an aqueous solution of an alkaline metal hydroxide or carbonate. The appropriate amount of phase-transfer reactant is added and the entire mixture is heated at the desired temperature for a length of time sufficient to ensure complete or substantially complete reaction. The diphenyl ether which is formed is recovered by suitable means, for example, by filtration.

The examples given below are by way of illustration and are not intended to limit our invention thereto. In each of these examples the reaction was conducted in an autoclave, since the reaction temperature exceeded the boiling point of water.

EXAMPLE 1

A mixture of 0.5 mole each of p-nitrochlorobenzene (79.0 g), p-hydroxyanisole (62.0 g), and potassium hydroxide (33.0 g, 86% pure), in 100 ml water was heated at 140° C. for about 3.5 hours. The resulting solid, collected by filtration, had a melting point of 100°–107° C. Reactants were further removed from the crude product by steam distillation, and the remaining solid was washed with copious amounts of water to afford a brown, granular mass of 4-methoxy-4'-nitrodiphenyl ether (83 g, 68% yield).

EXAMPLE 2

In this reaction 0.25 mole of each reactant was employed. A mixture of 39.5 g p-nitrochlorobenzene, 31.0 g p-hydroxyanisole, and 16.5 g potassium hydroxide in 50 ml water was mixed with 10 mole percent (16 g) of the phase-transfer reagent JETQUAT C-50, a 50% solution of $(C_{16}H_{33})N^+(CH_3)_3N^+Cl^-$ supplied by Deep Valley Chemical Co. The mixture was heated at 135° C. for three hours. Upon cooling the solids were collected by filtration and washed well with water to afford 60 g of a crystalline brown product (98% yield) of melting point 108°–111° C.

Thus the addition of the phase-transfer reagent afforded product in nearly quantitative yield and of sufficiently high purity that it could be used directly in subsequent reactions without detriment.

EXAMPLE 3

A mixture of 0.25 mole each of 2-methoxyphenol, 2-nitrobromobenzene, and potassium hydroxide in 50 ml. water containing 5 mole percent benzyltrimethylammonium chloride may be heated at 100°–150° C. for about four hours. The solids which form upon cooling may be removed by filtration and washed with copious amounts of water to yield over 90% of 2-methoxy-2'-nitrodiphenyl ether.

EXAMPLE 4

A mixture of 0.2 mole each of 4-nitrophenol, 2,4-dinitrochlorobenzene, and sodium carbonate in 70 ml. of water containing about 3 mole percent of mixed quaternary ammonium chloride of the formula $(C_8-C_{12})_3N^+CH_3Cl^-$ may be heated at about 150° C. for about five hours. After the mixture has cooled, solid may be removed by filtration to afford an excellent yield of 2,4,4'-trinitrodiphenyl ether.

What is claimed is:

1. A method for the preparation of a nitro-substituted diphenyl ether which comprises reacting an alkali metal salt of phenol possessing at least one moiety on the ring of said phenol selected from the group consisting of alkyl, aryl, alkaryl, hydroxy, alkoxy, aryloxy, amino, alkylamino, dialkylamino, nitro and alkylthio moieties with a nitrosubstituted halobenzene having the halo moiety substituted to the aromatic ring of said nitro-substituted halobenzene to effect the arylation of said phenol in the presence of a phase-transfer agent represented by the formula $$R_1R_2R_3R_4Z^+Y^-$$

wherein R is equal to an alkyl or aralkyl moiety possessing from 1 to 20 carbon atoms, Z is equal to nitrogen or phosphorous and Y is a halide, at a reaction temperature of about 50° to about 200° C. for a period of time equivalent to about 0.5 to about 20 hours.

2. The method of claim 1 wherein said phenol is selected from the group consisting of 4-methoxyphenol, 2-methoxyphenol, 4-nitrophenol and 2-nitrophenol, and said nitro-substituted halobenzene is 4-nitrohalobenzene.

3. The method of claim 2 wherein said nitro-substituted halobenzene is 2-nitrohalobenzene.

4. The method of claim 2 wherein said nitro-substituted halobenzene is 2,4-dinitrohalobenzene.

5. The method of claim 1 wherein the phase-transfer reactant is used at a concentration from about 1 to about 50 mole percent.

* * * * *